(12) United States Patent
Van Weerd et al.

(10) Patent No.: US 9,550,345 B2
(45) Date of Patent: Jan. 24, 2017

(54) PROCESS FOR THE PREPARATION OF AN OBJECT SUPPORTING A LIPID BILAYER

(71) Applicant: UNIVERSITEIT TWENTE, Enschede (NL)

(72) Inventors: Jasper Van Weerd, Enschede (NL); Hermanus Bernardus Johannes Karperien, Enschede (NL); Pascal Jonkheijm, Enschede (NL)

(73) Assignee: UNIVERSITEIT TWENTE, Enschede (NL)

(*) Notice: Subject to any disclaimer, the term of this patent is extended or adjusted under 35 U.S.C. 154(b) by 0 days.

(21) Appl. No.: 14/890,982

(22) PCT Filed: May 16, 2014

(86) PCT No.: PCT/EP2014/060173
§ 371 (c)(1),
(2) Date: Nov. 13, 2015

(87) PCT Pub. No.: WO2014/184383
PCT Pub. Date: Nov. 20, 2014

(65) Prior Publication Data
US 2016/0096920 A1    Apr. 7, 2016

(30) Foreign Application Priority Data
May 16, 2013 (EP) .................... 13168108

(51) Int. Cl.
| | | |
|---|---|---|
| B32B 27/06 | (2006.01) |
| B32B 17/06 | (2006.01) |
| B32B 15/04 | (2006.01) |
| B32B 18/00 | (2006.01) |
| B32B 27/36 | (2006.01) |
| A61L 27/18 | (2006.01) |
| A61L 27/34 | (2006.01) |
| A61L 27/54 | (2006.01) |
| C08G 63/91 | (2006.01) |

(52) U.S. Cl.
CPC .............. *B32B 27/06* (2013.01); *A61L 27/18* (2013.01); *A61L 27/34* (2013.01); *A61L 27/54* (2013.01); *B32B 15/04* (2013.01); *B32B 17/06* (2013.01); *B32B 18/00* (2013.01); *B32B 27/36* (2013.01); *C08G 63/912* (2013.01); *C08G 63/916* (2013.01)

(58) Field of Classification Search
CPC ..... C08G 63/912; C08G 63/916; A61L 27/18; A61L 27/34; A61L 27/54; B32B 27/06; B32B 27/36; B32B 18/00; B32B 15/04; B32B 17/06
See application file for complete search history.

(56) References Cited

U.S. PATENT DOCUMENTS

| | | |
|---|---|---|
| 4,661,235 A | 4/1987 | Krull et al. |
| 5,919,576 A | 7/1999 | Hui et al. |
| 5,922,161 A | 7/1999 | Wu et al. |
| 5,922,594 A | 7/1999 | Lofas |
| 6,294,614 B1 | 9/2001 | Kataoka et al. |
| 6,541,071 B1 | 4/2003 | Bookbinder et al. |
| 6,940,580 B2 | 9/2005 | Winterton et al. |
| 7,329,415 B2 | 2/2008 | Lally et al. |
| 7,368,127 B2 | 5/2008 | Diana |
| 7,858,375 B2 | 12/2010 | Zhu et al. |
| 7,879,444 B2 | 2/2011 | Jiang et al. |
| 7,901,706 B2 | 3/2011 | Lally et al. |
| 8,197,841 B2 | 6/2012 | Linhardt et al. |
| 8,268,381 B2 | 9/2012 | Whiteford et al. |
| 8,377,464 B2 | 2/2013 | Linhardt et al. |
| 2004/0096914 A1 | 5/2004 | Fang et al. |
| 2007/0120279 A1 | 5/2007 | Linhardt et al. |
| 2007/0122540 A1 | 5/2007 | Salamone et al. |
| 2008/0094573 A1 | 4/2008 | Vermette et al. |
| 2008/0241942 A1 | 10/2008 | Zhu et al. |
| 2011/0159273 A1* | 6/2011 | Lukowski ................ A61L 2/14 428/323 |

FOREIGN PATENT DOCUMENTS

| | | |
|---|---|---|
| EP | 0784793 A1 | 7/1997 |
| EP | 1262307 A2 | 4/2002 |
| EP | 1485067 A2 | 12/2004 |
| EP | 1583568 A2 | 10/2005 |
| EP | 1828813 A1 | 9/2007 |
| EP | 2653155 A1 | 10/2013 |
| EP | 2746835 A1 | 6/2014 |
| WO | 9610178 A1 | 4/1996 |
| WO | 9638726 A1 | 12/1996 |
| WO | 9702310 A1 | 1/1997 |
| WO | 0016623 A1 | 3/2000 |
| WO | 0170419 A1 | 9/2001 |
| WO | 02072873 A1 | 9/2002 |
| WO | 03011821 A2 | 2/2003 |
| WO | 2004044585 A1 | 5/2004 |
| WO | 2004111185 A2 | 12/2004 |
| WO | 2008059502 A2 | 5/2008 |
| WO | 2009133461 A1 | 11/2009 |
| WO | 2010096558 A1 | 8/2010 |
| WO | 2010147779 A2 | 12/2010 |
| WO | 2011085326 A1 | 7/2011 |
| WO | 2011102356 A1 | 8/2011 |
| WO | 2012151554 A1 | 11/2012 |
| WO | 2012173796 A2 | 12/2012 |
| WO | 2013090801 A1 | 6/2013 |
| WO | 2014039013 A1 | 3/2014 |
| WO | 2014078801 A1 | 5/2014 |
| WO | 2014191316 A1 | 12/2014 |
| WO | 2015000534 A1 | 1/2015 |

OTHER PUBLICATIONS

Gupta, B., et al.; Journal of Applied Polymer Science, 2000, p. 1083-1091.*
Mourtas, S., et al.; Colloids and Surfaces B: Biointerfaces, 2011, p. 214-220.*

* cited by examiner

*Primary Examiner* — Robert Jones, Jr.
(74) *Attorney, Agent, or Firm* — Hudak, Shunk & Farine Co. LPA

(57) ABSTRACT

A process for the preparation of an object, supporting a lipid bilayer, for use in tissue engineering including the steps of providing an object having a surface, treating the surface of the object with a plasma containing active oxygen to provide the surface of the object with reactive groups A, to provide the surface of the object with reactive groups A, covalently attaching a sterol group to the reactive groups A and contacting the object activated with sterol groups with a lipid solution to form a lipid bilayer.

16 Claims, 2 Drawing Sheets

PROCESS FOR THE PREPARATION OF AN OBJECT SUPPORTING A LIPID BILAYER

FIELD OF THE INVENTION

The invention is directed to a process for the preparation of an object and to an object supporting a lipid bilayer.

BACKGROUND OF THE INVENTION

Bio-compatible materials have been developed extensively and used in in vivo applications. However, bio-compatibility does not imply proper cell response upon implantation of the material. Hence a majority, if not all, of the bio-compatible materials display a certain degree of bio-inertness limiting their use and/or performance. Bio-inertness encompasses the lack of proper interaction with the host tissue, either caused by the chemically inert surface, absence of biological triggers or (bio)fouling through bulk protein absorption. This lack of proper interaction occurs rapidly upon implantation of a material and disturbs specific cell interaction. Bio-inertness has been tackled by the modification of surface architecture and topology and by incorporating bio-active ligands via covalent or non-covalent chemistry to bio-compatible materials to provoke desired cell responses. Model cell membranes, like Supported Lipid Bilayers (SLB), have shown great promise in reducing protein fouling and are tuneable in their surface composition. SLBs can be prepared via vesicle fusion and have been widely used since they were first reported (McConnel and Tamm 1985). The non-fouling nature of SLBs and their tuneable composition makes them an ideal candidate to serve as a surface coating on solid materials. However, the use of SLBs in in vivo applications has been limited.

SLBs are for example described in US2008/0241942. In this document a method for fabricating supported lipid bilayer membranes is described. The bilayer is applied on a solid surface; preferably an array. The method comprises the following steps: (i) providing a solid surface coated with a molecular film; (ii) covalently attaching sterol groups to the molecular film and (iii) contacting the sterol functionalized molecular film with a lipid solution. A disadvantage of the method described in US2008/0241942 is that a molecular film, which is for instance a hydrophilic polymer or a hydrogel coating, has to be applied to the solid surface to be able to attach a bilayer. The bilayer is not directly attached to the surface of the object, but only through the molecular film attached to the solid surface. The molecular film contains reactive groups that will covalently react with sterol groups, which will be converted into the SLB. After the reaction between sterol groups and functional groups in the molecular films, residual functional groups will be present in the hydrogel, which may destabilize the SLB, and give unwanted complications. Moreover the application of the molecular film on the support is an additional step, which is time consuming, but also adds to the complexity of the system. Not only the preparation of the SLB needs to be controlled, but also the interaction and adhesion between the substrate and the molecular film, and the stability of the molecular film. Further, the molecular film cannot be applied on all types of solid surfaces. Therefore limitations exist on the choice of substrate to be used for making a SLB. Another disadvantage is that by the application of the molecular film the chemical and mechanical properties of the solid surface are changed.

There is a need for an improved method to produce a lipid bilayer on a wide variety of bio-compatible materials.

SUMMARY OF THE INVENTION

The present invention solves this by providing a process for the preparation of an object, supporting a lipid bilayer, for use in tissue engineering comprising the steps of providing an object having a surface, treating the surface of the object with a plasma containing active oxygen to provide the surface of the object with reactive groups A, covalently attaching a sterol group to the reactive groups A and contacting the object activated with sterol groups with a lipid solution to form a lipid bilayer.

The process according to the invention provides for easy, straightforward and cheap surface modification of an object for use in tissue engineering without affecting the bulk properties thereof.

Another advantage of the process according to the invention is that an air stable lipid bilayer can be formed on the object.

Further, the process can be easily adjusted for the treatment of objects made of different kinds of materials.

A further advantage is that the object obtained with the process according to the invention is suitable for in vivo use.

A further advantage is that the process is applicable to objects, made of a wide variety of materials with distinct chemical and mechanical properties, that can be introduced in the body and that cell response to these objects is independent of the chemical and mechanical properties thereof.

With the process according to the invention an object for use in tissue engineering is prepared. The object provides one or more surfaces to support a lipid bilayer. The surfaces are preferably uncoated. Examples of materials that can be used to prepare the object are metal, e.g. titanium, aluminum, platinum; metal oxides, alloy, glass, ceramic or polymeric materials and combinations of these materials. The polymeric materials can be homopolymers, copolymers or block copolymers. Examples of polymeric materials are polyurethane, polyacrylate, polystyrene, polycarbonate, polyethyleneterephtalate (PET) polybutyleneterephtalate (PBT), polyethyleneoxide (PEO), polyethersulfone (PES), polytetra-fluoroethylen (PTFE), polytrimethylenecaprolactone (PTMC), polyanhydride, polylactic acid (PLA), poly (ortho)ester and polyphosphazene. The object preferably comprises a polyester, more preferably a polycaprolactone. The object preferably is made of a bio-compatible material.

The object can have a two-dimensional or a three-dimensional structure. A two-dimensional object can, for instance, be a film or a mesh. These two-dimensional objects can, for instance, repair or replace skin. A three-dimensional object can, for instance, be an implant or a device. The implant is, for example, designed to repair or replace bone, cartilage or a blood vessel in a human or animal body. The device is, for example, a device that can be used during treatment or healing of a human or animal body.

The object can be prepared by using molding, compounding, extrusion, film blowing or casting or other methods. Also rapid prototyping or electro-spinning can be used to prepare the objects.

The surface of the object is treated with a plasma containing active oxygen. Active oxygen comprises a mixture of highly reactive oxygen containing compounds. Active oxygen can comprise ozone. By the treatment with the plasma containing active oxygen the surface of the object is modified. The active oxygen only modifies the surface of the object; the bulk properties of the object are not affected.

A plasma treatment of the surface of the object can be performed in various commercially available plasma generators. The plasma generators can, for example, comprise a source for providing electromagnetic radiation. A plasma containing active oxygen can be obtained by using the electromagnetic radiation to activate an oxygen-containing gas. The oxygen-containing gas can, for example, be air or an oxygen enriched gas, for example containing at least 50% oxygen, or at least 75% oxygen or at least 90% oxygen.

The energy of the electronic radiation that forms the plasma can vary between wide limits, but preferably is between 50 J and 800 J, more preferably between 100 J and 700 J and most preferably between 200 J and 600 J.

The plasma containing active oxygen can be obtained, for instance, by corona treatment. Corona treatment (also referred to as air plasma) is a surface modification technique that uses a low temperature corona discharge plasma to impart changes in the properties of a surface. The corona plasma is generated by the application of high voltage to sharp electrode tips which forms plasma at the ends of the sharp tips. A linear array of electrodes is often used to create a curtain of corona plasma. This is the most common type of plasma generator for industrial use, which is cost-effective and does not require an oxygen source other than the ambient air to produce active oxygen concentrations of 3-6%.

The plasma containing active oxygen can also be created by ultra-violet (UV) light, radio frequency (RF) plasma, cold plasma treatment or electrolytic generation of active oxygen. UV generators, or vacuum-ultraviolet (VUV) generators, employ a light source that generates a narrow-band ultraviolet light and produce plasma with an active oxygen concentration of about 0.5% or lower. A disadvantage of this method is that it requires the air (oxygen) to be exposed to the UV source for a relatively long amount of time. In the cold plasma method, a plasma is created by the exposure of pure oxygen gas to a dielectric barrier discharge. The diatomic oxygen is split into single atoms. The oxygen atoms can, for example, recombine in triplets to form ozone. Cold plasma machines preferably utilize pure oxygen (for example comprising more than 75% oxygen), as the input source and produce a plasma with a maximum concentration of about 5% active oxygen. Electrolytic generation of plasma containing active oxygen splits water molecules in the plasma into, for example, $H_2$, $O_2$, and $O_3$. In most electrolytic generation methods, the hydrogen gas will be removed to leave the remaining gases, comprising for example oxygen and ozone as the only reaction products in the plasma. This method of generation of a plasma containing active oxygen can achieve concentrations of 20-30% of active oxygen in the plasma and is independent of air quality because water is used as the starting substrate.

Preferably, RF plasma treatment or cold plasma treatment is used to treat the surface of the object with a plasma containing active oxygen.

In an embodiment of the invention the plasma generator can comprise an activation chamber, wherein the object can be treated. The activation chamber can be under reduced pressure during the plasma treatment. The reduced pressure preferably is a pressure below 1 bar, more preferably below 10 Torr, most preferably below 1 Torr. According to this embodiment the activation chamber is fed with an oxygen-containing gas that can be activated by the electromagnetic radiation to form the plasma containing the active oxygen.

Reactive groups A are formed on the surface of the object by the treatment with plasma containing active oxygen. Examples of these reactive groups A are hydroxyl, aldehyde, ester and acid groups. Preferably, the reactive groups A on the surface are aldehyde groups. The reactive groups A are not stable and will disappear over time. The stability of the reactive groups A is relatively large when kept under a polar solvent like for example water or an alcohol. At room temperature the reactive groups A may be stable up to 200 hours after plasma treatment. Under hydrophobic conditions like for example an apolar solvent or a gas, the stability is limited. At room temperature under hydrophobic conditions, the reactive groups may be stable for only a few hours, like for example 2 hours, or even less.

The presence of the reactive groups A on the surface of the object is of course essential for the possibility to form covalent bonds with the sterol groups. Preferably, covalently attaching the sterol groups should take place at most 2 hours after the treatment of the surface of the object with plasma, more preferably at most 1.5 hours after the treatment, most preferably at most 1 hour after the treatment. Normally, covalently attaching of the sterol groups takes place within 30 minutes, preferably within 15 minutes after the treatment.

The concentration of reactive groups A on the surface of the object is influenced by the amount of active oxygen that is present in the plasma and the time the object is exposed to active oxygen. The amount of active oxygen in the plasma can vary within wide limits and is, for example, dependent on the method that is chosen for the plasma treatment, the energy of the electronic radiation that forms the plasma and the conditions in the activation chamber during plasma treatment.

The amount of active oxygen in the plasma that is needed to create reactive groups A on the surface of the object varies with the type of object, the material of the object and the properties of the material that is used to make the object.

For example, when the object is made of polycaprolactone and a corona treatment is chosen the treatment the plasma can be formed with electronic radiation with an energy of 400 J and can last from 1-10 seconds, preferably from 2-6 seconds. When UV treatment is chosen for the treatment of the same object the plasma can be formed with electronic radiation with the same energy and can last from 10-7200 seconds, preferably from 15-3600 seconds. When a RF plasma or a cold plasma method is used to treat the object the plasma can be formed with electronic radiation with an energy of 400 J and the treatment can last from 5 to 12 seconds, preferably between 6-11 seconds.

The amount of reactive groups A on the surface of the object can be determined by X-ray photoelectron spectroscopy (XPS) and is at least 0.02 $nm^{-2}$, preferably at least 0.06 $nm^{-2}$ and more preferably at least 0.15 $nm^{-2}$. The amount of reactive groups A is preferably at most 10 $nm^{-2}$, more preferably at most 5 $nm^{-2}$ and most preferably at most 2 $nm^{-2}$. Preferably, the amount of reactive groups A is between 0.15 and 2 $nm^{-2}$. The amount of reactive groups A is given in $nm^{-2}$, which represents the amount of reactive groups A per $nm^2$ of the surface of the object. According to the process of the invention a sterol group is covalently attached to the reactive groups A. Preferred sterol groups are cholesterol, desmosterol, campesterol, lanosterol, sitosterol, stigmasterol and ergosterol. More preferably, the sterol group is cholesterol. The sterol can react directly with the reactive group A through the hydroxyl group at the 3-position of the A-ring, or through a spacer moiety. In a preferred embodiment of the invention, the sterol group has a spacer moiety, which spacer moiety can covalently react with the reactive groups A on the surface of the object. The sterol having a spacer moiety can be prepared from a sterol and a spacer. The spacer comprises preferably one reactive group B and one reactive group C. Reactive groups B can covalently react with the hydroxyl group of the sterol and reactive groups C can covalently react with reactive groups A on the surface of the object. In this way the sterol can be covalently attached to reactive group A via a spacer moiety. The spacer preferably comprises a hydrocarbon group having 1 to 50 carbon atoms, preferably 1-20 carbon atoms, more preferably 1-10 carbon atoms. The spacer can also comprise heteroatoms, such as for instance oxygen, sulfur and nitrogen. Examples of spacers are polyamines, for instance spermine, peptides and hydrophilic polymers or oligomers. Preferably, the spacer is a hydrophilic polymer or oligomer, more preferably the spacer comprises a polyether, most preferably an oligo(ethyleneglycol).

Preferably the reactive groups B and C are attached to the extreme ends of the spacer. Examples of reactive groups B and C are amines, amides, carboxylic acids and esters.

The amount of sterol groups on the surface of the object is important. The amount of sterol groups can be determined by X-ray photoelectron spectroscopy (XPS) and is at least $0.02$ $nm^{-2}$, preferably at least $0.05$ $nm^{-2}$ and more preferably at least $0.1$ $nm^{-2}$. The amount of sterol groups is preferably at most $5$ $nm^{-2}$, more preferably at most $2$ $nm^{-2}$ and most preferably at most $1$ $nm^{-2}$. The amount of sterol groups is given in $nm^{-2}$, which represents the amount of sterol groups per $nm^2$ of the surface of the object.

If the amount of sterol groups is too low the lipid vesicles in the lipid solution will not unfold to form a lipid bilayer or an unstable lipid bilayer will be formed. If the amount of sterol groups on the object is too high only a lipid monolayer and not a lipid bilayer will form on the object or lipid bilayer is formed wherein the lower layer is not a mobile layer.

The amount of sterol groups on the surface of the object will, in general, be lower than the amount of reactive groups A, because the reactive groups A are not stable and a part of the reactive groups A will disappear over time.

The incubation time of the object activated with reactive groups A with the sterol groups is important. The sterol groups must have enough time to react with the reactive groups A. At room temperature the incubation time of the sterol groups, preferably is between 0.25 and 4 hours, more preferably between 0.5 and 3 hours, most preferably between 0.75 and 2.5 hours.

According to the process of the invention the object activated with sterol groups is contacted with a lipid solution to form a lipid bilayer. Because the sterol groups are present on the complete surface of the object the lipid bilayer will be present around the total object. An advantage of the process according to the invention is that the lipid bilayer follows the surface of the object closely. In this way also objects with complex structures can be coated with a lipid bilayer.

The lipid solution can be a solution of synthetic or naturally occurring lipids and amphiphilic molecules, such as phospholipids, sphingolipids, ceramides and sterols. The lipid solution may contain vesicles, liposomes, micelles and monolayer or bilayer membrane fragments. The lipid solution may further contain trans-membrane proteins, peripheral membrane proteins, peptides and glycolipids. A mixture of different lipids can be used. Specific examples of suitable lipids are phospholipids, which can be natural or synthetic. Natural phospholipid derivates are, for example, egg phosphatidylcholine (PC), egg phosphatidylglycerol (PG), soy PC, hydrogenated soy PC and sphingomyelin.

Examples of synthetic phospholipid derivates are:
Phosphatidic acid derivatives, for example 1,2-Dimyristoyl-sn-glycero-3-phosphate (DMPA), 1,2-Dipalmitoyl-sn-glycero-3-phosphate (DPPA), 1,2-Distearoyl-sn-glycero-3-phosphate (DSPA)
Phosphatidylcholine derivatives, for example 1,2-Didecanoyl-sn-glycero-3-phosphocholine (DDPC), 1,2-Dilauroyl-sn-glycero-3-phosphocholine (DLPC), 1,2-Dimyristoyl-sn-glycero-3-phosphocholine (DMPC), 1,2-Dipalmitoyl-sn-glycero-3-phosphocholine (DPPC), 1,2-Distearoyl-sn-glycero-3-phosphocholine (DSPC), 1,2-Dioleoyl-sn-glycero-3-phosphocholine (DOPC), 1-Palmitoyl-2-oleoyl-sn-glycero-3-phosphocholine (POPC), 1,2-Dierucoyl-sn-glycero-3-phosphocholine (DEPC)
Phosphatidylglycerol derivatives, for example 1,2-Dimyristoyl-sn-glycero-3[Phospho-rac-(1-glycerol) (DMPG), 1,2-Dipalmitoyl-sn-glycero-3[Phospho-rac-(1-glycerol) (DPPG), 1,2-Distearoyl-sn-glycero-3[Phospho-rac-(1-glycerol) (DSPG), 1-Palmitoyl-2-oleoyl-sn-glycero-3[Phospho-rac-(1-glycerol)](POPG)
Phosphatidylethanolamine derivatives, for example 1,2-Dimyristoyl-sn-glycero-3-phosphoethanolamine (DMPE), 1,2-Dipalmitoyl-sn-glycero-3-phosphoethanolamine (DPPE), 1,2-Distearoyl-sn-glycero-3-phosphoethanolamine (DSPE), 1,2-Dioleoyl-sn-glycero-3-phosphoethanolamine (DOPE).
Phosphatidylserine derivatives, for example 1,2-Dioleoyl-sn-glycero-3-phosphoserine (DOPS)
PEG phospholipid derivatives, for example (mPEG-phospholipids, polyglycerin-phospholipids, funcitionalized-phospholipids, terminal activated-phospholipids) and N-[1-(2,3-Dioleoyloxy)propyl]-N,N,N-trimethylammonium methyl-sulfate (DOTAP).

Phospholipids have a hydrophilic head and two hydrophobic tails each. When phospholipids are exposed to water, they arrange themselves into a two-layered sheet (a bilayer) with all of their tails pointing towards the center of the sheet. The center of this bilayer contains almost no water and excludes molecules like sugars or salts that dissolve in water but not in oil.

At a given temperature a lipid bilayer can exist in either a liquid or a gel (solid) phase. All lipids have a characteristic temperature at which they transition (melt) from the gel to the liquid phase. In both phases the lipid molecules are prevented from flip-flopping across the bilayer, but in liquid phase bilayers a given lipid will exchange locations with its neighbor millions of times a second. Unlike liquid phase bilayers, the lipids in a gel phase bilayer are locked in place.

While lipid tails primarily modulate bilayer phase behavior, it is the head group of the lipid that determines the bilayer surface chemistry. Of the phospholipids, the most common head group is phosphatidylcholine (PC). Phosphatidylcholine is a zwitterionic head group, as it has a negative charge on the phosphate group and a positive charge on the amine but, because these local charges balance, no net charge is present at physiological pH. Another example of a head group with no net charge at physiological pH is phosphatidylethanolamine.

Other head groups, such as for example, phosphatidic acid, phosphatidylserine and phosphadidyl glycerol carry a negative charge at physiological pH.

Due to their zwitterionic nature, phosphatidylcholine derivatives are preferably used; more preferably the phosphatidylcholine derivatives 1,2-Dioleoyl-sn-glycero-3-phosphocholine (DOPC), 1,2-Dipalmitoyl-sn-glycero-3- phosphocholine (DPPC) and 1,2-Distearoyl-sn-glycero-3-phosphocholine (DSPC) are used.

The solvent normally is an aqueous solution, such as, for example, an aqueous buffer or salt solution.

The lipid bilayer can be crosslinked. Crosslinking of a lipid bilayer can be achieved under UV light. This initiates the photopolymerization of, for example, dienoyl (Den), diacetylene (Diyne), sorbyl (Sorb) or acryloyl containing lipids. Examples of the these lipids are, bis-DenPC, mono-DenPC, mono-SorbPC and bis-SorbPC, Diyne phosphatidylethanolamine (PE). Additional crosslinking can also be achieved via the use of fatty acid modified lipids, such as for example, diacetylene lipids, for example 1,2-bis(10,12-tricosadiynoyl)-sn-glycero-3-phosphoethanolamine, or diphytanoyl lipids, for example, 1,2-di-O-phytanyl-sn-glycero-3-phosphoethanolamine.

In a next step of the process according to the invention the lipid bilayer is contacted with a peptide comprising at least one hydrophobic tail. Peptides are short chains of amino acid monomers linked by peptide bonds, the covalent chemical bonds formed when the carboxyl group of one amino acid reacts with the amino group of another. Peptides are distinguished from proteins on the basis of size and contain about 50 amino acids or less. The peptides can, for example, be chosen from fragments of proteins or recombinant proteins. The peptide is preferably a fibronectin derived peptide; more preferably RGD or PHSRN. RGD is an abbreviation of arginylglycylaspartic acid which is a tripeptide composed of L-arginine, glycine, and L-aspartic acid. PHSRN is an abbreviation for the peptide sequence Pro-His-Ser-Arg-Asn. Wherein Pro, His, Ser, Arg and Asn are abbreviations for amino acids and Pro is proline, His is histidine, Ser is serine, Arg is arginine and Asn is asparagine. The peptide comprises at least one hydrophobic tail, preferably one or two hydrophobic tails. Examples of the hydrophobic tails are palmitoyl, myristoyl, geranyl, farnesyl, glycosyl, phosphatidyl and inositol groups. Preferably the peptide comprises at least one palmitoyl hydrophobic tail. More preferably, the peptide comprises one or two palmitoyl hydrophobic tails. The hydrophobic tail(s) connect with the hydrophobic inner part of the lipid bilayer. It is believed that the peptides that are connected with the lipid bilayer influence the cell attachment and the cell function of cells that make contact with the object supporting a lipid bilayer.

The peptide comprising a hydrophobic tail can also be mixed with the lipid solution and, together with the lipid solution, be contacted with an object that is modified with sterol groups.

In one preferred embodiment, the process according to the invention comprises the steps of providing an object from polycaprolactone having a surface, treating the surface of the object with an oxygen containing RF plasma or cold plasma to provide the surface of the object with reactive groups A, reacting a sterol group comprising a cholesterol covalently attached to an oligo(ethyleneglycol) spacer with reactive group A, contacting the object activated with cholesterol groups with a lipid solution comprising a phosphatidylcholine derivative to form a lipid bilayer, and contacting the lipid bilayer with the peptide RGD or PHSRN comprising one or two palmitoyl hydrophobic tails.

In another embodiment the invention is also directed to an object supporting a lipid bilayer comprising an object comprising a polyester material, sterol groups covalently attached via a spacer to the polyester material, a lipid bilayer surrounding the sterol groups that are covalently attached to the polyester material and peptides comprising at least one hydrophobic tail attached to the lipid bilayer.

In the object according to the invention the polyester preferably is polycaprolactone. The spacer can be selected from the spacers as discussed here above. The spacer preferably comprises an oligo(ethyleneglycol). The oligo-ethyleneglycol comprises preferably between 1 and 20 ethylene glycol monomer units, more preferably between 2 and 10 units, most preferably between 2 and 6 units. The lipid bilayer can comprise any of the lipids as discussed above. The lipid bilayer preferably comprises a phospholipid, more preferably a phosphatidylcholine derivative, more preferably DOPC. The peptides comprising at least one hydrophobic tail preferably comprise at least one palmitoyl hydrophobic tail. The peptide is preferably a fibronectin derived peptide; more preferably RGD or PHSRN; most preferably the peptide is a palmitoylated RGD or PHSRN.

The objects supporting a lipid bilayer according to the invention can be used in tissue engineering, where specific cell interaction is needed to enable proper tissue formation. Tissue engineering occurs on the object supporting the lipid bilayer as produced with the process of the invention. The tissue engineering can occur in vivo, in vitro or ex vivo. The invention enables the decoupling of the properties of the bulk material of the object from the surface cell response. As a result the object is able to simultaneously address the bio-inertness of implantable materials and provide customizable cell interaction. By changing the composition of the bilayer the state (liquid or gel, positively, negatively or not charged) of the bilayer on the object can be influenced. This will have an influence on cell adhesion and cell growth on the surface of the bilayer. Thus, by changing the composition of the bilayer tissue engineering on an object can be influenced and steered.

An example of tissue engineering is tissue regeneration, wherein cartilage, blood vessels or heart valves are cultured for transplantation purposes.

The objects according to the invention also have antifouling properties.

The invention will hereafter be elucidated by way of the following examples, without being limited thereto.

DETAILED DESCRIPTION OF THE INVENTION

Examples

Example I

Synthesis of the Sterol Group

Figure 1:
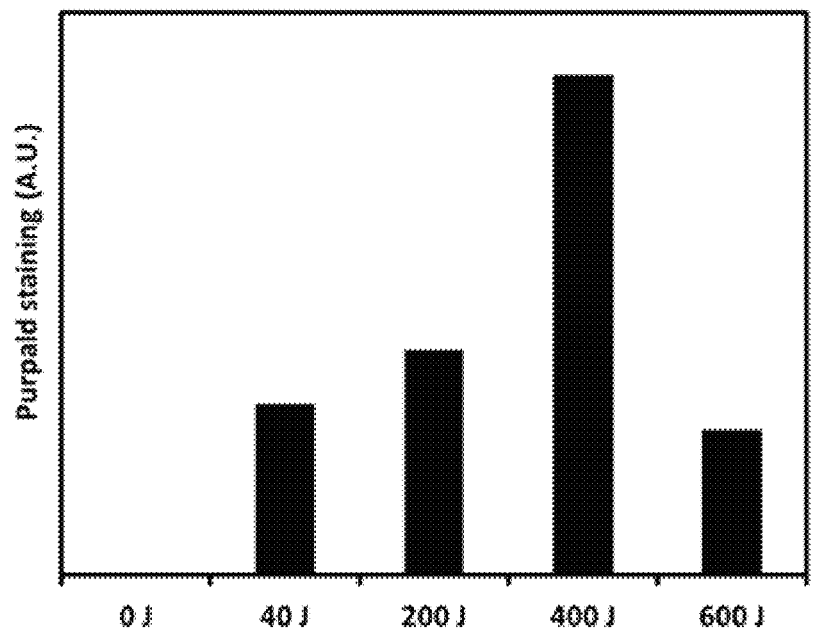
FIG. 1 shows the effect of plasma energy on the formation of aldehyde groups (after purpald staining)

Synthesis of an amine terminated cholesterol group was based on literature.

To a stirred solution of 1.0 molar equivalent i (n-Boc-2,2'-[ethylenedioxy]diethylamine, Sigma-Aldrich) and 1.1 molar equivalents ii (cholesteryl chloroformate, Sigma-Aldrich) in anhydrous toluene, 1.5 molar equivalents of DIPEA (diisopropylethylamine, Sigma-Aldrich) and a catalytic amount of DMAP (4-Dimethylaminopyridine, Sigma-Aldrich) were added. The reaction mixture was refluxed under argon atmosphere for 17 hours. Subsequently, the solvent was removed under reduced pressure to obtain an oily residue. Flash column chromatography was performed using 40% ethyl acetate+60% hexane as eluent (Rf=0.22).

The solvent was removed under reduced pressure and the product iii was found to be an off white sticky residue. ESI-TOF: [M]$^+$ calcd 661, [M]$^+$ found 661.

$^1$H NMR (300 MHz, CDCl$_3$): 5.37 (t, 1H, olefinic H), 5.25 (t, 1H, NH), 5.1 (t, 1H NH), 4.5 (m, 1H, O—CH cholesterol), 3.61 (s, 4H, O—CH$_2$—CH$_2$-0), 3.55 (m, 4H, 2×O—CH$_2$), 3.37 (m, 4H, 2×CH$_2$ in CH$_2$NH), 2.5-0.87 (34H, cholesterol), 1.5 (s, 9H tert BOC), 0.86 (d, 6H 2×CH$_3$ cholesterol), 0.68 (s, 3H, 1×CH$_3$ cholesterol).

Scheme 1 Schematic representation of a 3-step synthesis of an amine-terminated ethylene glycol spaced cholesterol group.

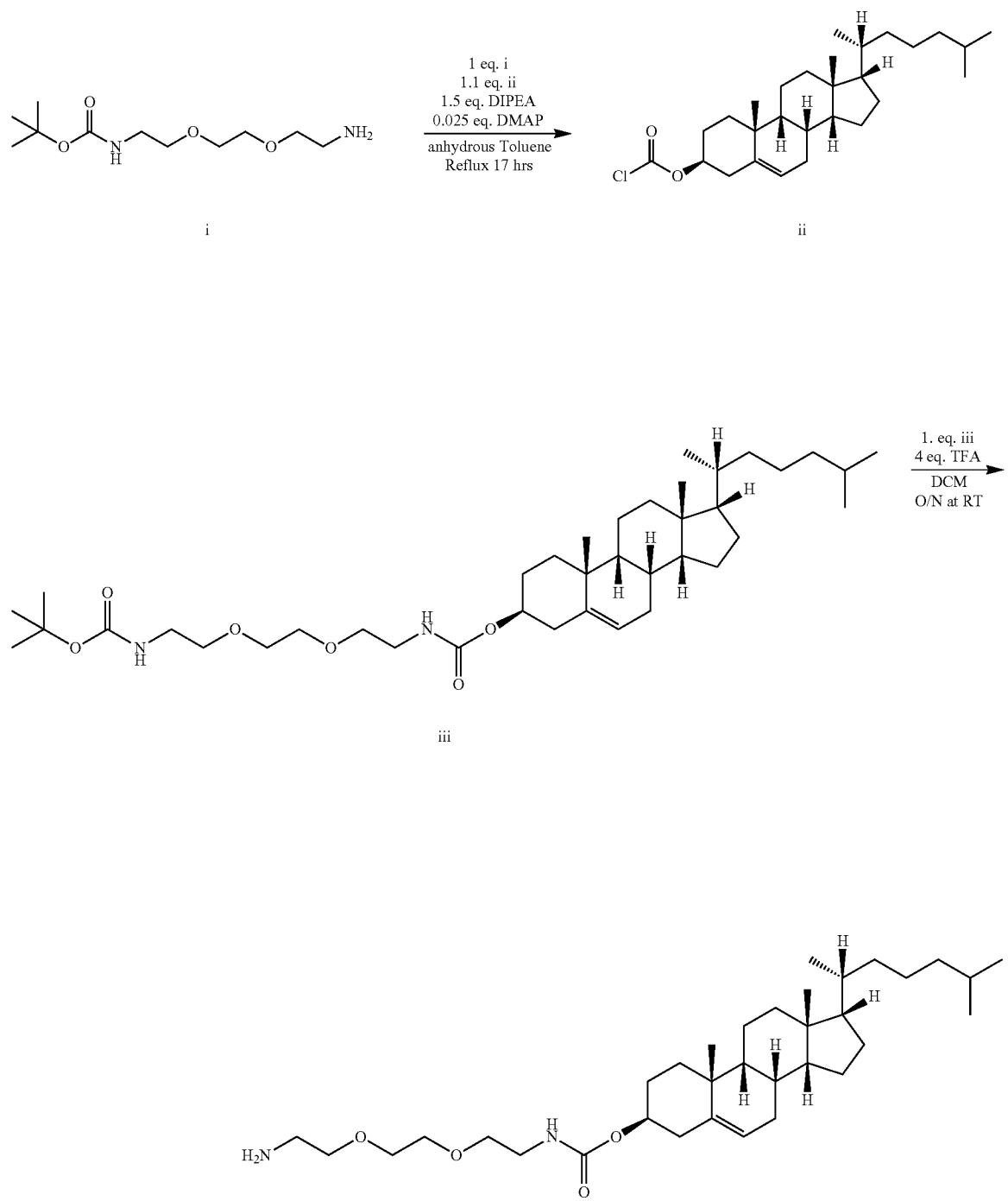

Product iii was dissolved in dichloromethane and was added in a drop-wise manner to a stirred solution of 4 molar equivalents of TFA (trifluoroacetic acid) in dichloromethane. Deprotection was obtained after 23 hours at room temperature under continuous stirring. Using TLC the deprotection was monitored. Solvent was removed under reduced pressure and the residue was dissolved in dichloromethane and neutralized with TEA (triethylamine). Flash column chromatography was performed using 1% $NH_3$ (aq) solution (25% $NH_3$ in water), 9% MeOH and 90% chloroform ($Rf_{frac13-16}$=0.38, $Rf_{frac17-35}$=0.24). After solvent removal a yellowish sticky residue was obtained (76.3% yield). The purified product was stored at −20° C. until further use.

ESI-TOF: $[M+H]^+$ calcd 561, $[M+H]^+$ found 561.

$^1$H NMR (300 MHz, $CDCl_3$): 5.37 (t, 1H, olefinic H), 5.25 (t, 1H NH), 4.5 (m, 1H, O—CH cholesterol), 3.61 (s, 4H, O—$CH_2$—$CH_2$—O), 3.56 (m, 4H, 2×$OCH_2$), 3.52 (t, 2H, $NH_2$), 3.37 (m, 2H, $CH_2$ in $CH_2NH$), 2.89 (t, 2H, $CH_2NH_2$), 2.5-0.87 (34H, cholesterol), 0.86 (d, 6H, 2×$CH_3$ cholesterol), 0.68 (d, 3H, 1×$CH_3$ Cholesterol)

Example II

Active Oxygen Treatment of Polycaprolactone

Polycaprolactone (PCL) was treated for ten seconds (10 s) with oxygen plasma treatment (OPT) using a Plasma prep II (SPI supplies). This is a RF plasma treatment. The PCL used was a PCL sheet solvent casted from chloroform, Mn 45,000 Da (Sigma).

Prior to sample treatment the chamber was cleaned during a 20 minutes cleaning run. The plasma treatment was performed using electromagnetic radiation having an energy of 400 J, at 200 mTorr of vacuum pressure.

This was sufficient to generate aldehyde groups as shown by the purple discoloration of aldehyde-specific Purpald dye in thin layer chromatography (TLC). The generation of aldehyde groups was further confirmed with X-ray photoelectron spectroscopy (XPS) and IR-spectroscopy. Quantera SXM (scanning XPS microprobe from Physical Electronics) showed an increase in oxygen bearing groups, in particular O—C=O and —C=O. Moreover, bulk polymer modification was excluded by comparing fourier transform infrared spectroscopy with attenuated total reflectance (FTIR-ATR; diamond) with Polarization Modulation Infrared Reflection Absorption Spectroscopy (PM-IRRAS). Only in PM-IRRAS on spin-coated gold samples a shoulder appeared in the carbonyl region that was not observed in the ATR spectra. Due to the differences in sampling depth, ATR diamond 5 µm and PM-IRRAS nm regime, surface confinement of the oxygen plasma treatment was concluded.

The plasma treatment was repeated with electromagnetic radiation having a different energy. The results of these experiments are given in FIG. 1. FIG. 1 clearly shows that there is an optimum in the energy of the electromagnetic radiation at 400 J for the treatment of PCL, under the present experimental conditions.

Example III

Surface Modification

The OPT modified polycaprolactone sheet according to example II was contacted with 1 mM of amine terminated cholesterol group in ethanol. Contacting lasted for 1 hour at room temperature while shaking the solution. The modified caprolactone sheet was reduced directly in a freshly made $NaBH_4$ solution (Sigma) i.e. 100 mg in 10 mL ethanol and 40 mL 1× Phosphate Buffered Saline (PBS, Sigma). In this example and in example IVa the PBS was prepared by the solution of a PBS tablet (Sigma) in 200 mL of deionized water to yield a 0.01 M phosphate buffered saline, with 0.0027 M potassium chloride and 0.137 M sodium chloride; pH 7.4 at 25° C. Subsequently the samples were rinsed with milliQ to remove salt and briefly sonicated in ethanol to remove adsorbed linker and dried under a stream of nitrogen.

To evaluate whether the aldehyde groups, formed after oxygen plasma treatment, are reactive towards the cholesterol group Time of Flight Secondary Ion Mass Spectroscopy (TOF-SIMS) (Waters-Micromass LCT) and contact angle measurements were used.

The surface modification of three different biopolymers treated with oxygen plasma treatment (OPT) using electromagnetic radiation having an energy of 400 J was compared. The biopolymers tested were polycaprolactone (PCL, Mn=45 kDa), a segmented block copolymer of poly(ethylene oxide terephthalate) and polybutylene terephthalate (PA, Polyactive® 1000/70/30) and a block copolymer of polylactic acid and polycaprolactone (PG, PLA65/PCL35). After the treatment with OPT the samples were incubated with the amine terminated cholesterol group for 1 hour as described above. After both the OPT treatment and the incubation with the amine terminated cholesterol group the sensile contact angle was determined.

The method for determining the contact angle was as follows:

The sensile water contact angle was measured using a Krüss contact angle measuring system G10. The sample for contact angle measurement was placed horizontally with the side to be measured facing up. Using the automated syringe a water droplet (30 µL droplet distilled or ultrapure milliQ water) was placed on the surface. The droplet was imaged within a period of 5 seconds. By the use of software fitting the sensile water contact angle with the sample surface was deduced. The samples were measured on multiple locations, >n=3, to ensure that a reliable value for the water contact angle was found.

Figure 2:
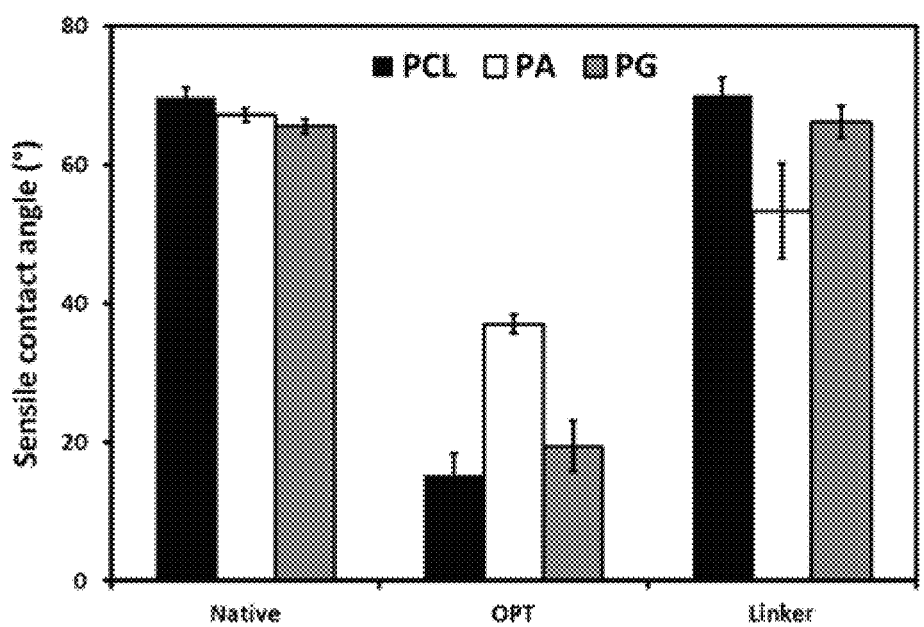
FIG. 2 shows the sensile contact angles for three types of native polymers (PCL, PA and PG), the contact angle after treatment with oxygen containing plasma and the contact angle after incubation with the amine terminated cholesterol group.

FIG. 2 shows the contact angle for the native polymers (PCL, PA and PG), the contact angle after treatment with OPT and the contact angle after incubation with the amine terminated cholesterol group. The contact angle becomes lower after the treatment with OPT which means that the surface becomes more hydrophilic. After incubation with the amine terminated cholesterol group the surface of the polymers becomes more hydrophobic again.

Further the contact angle after treatment with OPT was determined for the PG polymer. The contact angle was determined after various amounts of time as shown in Table 1. Also the mobility properties of the BSLB were determined. The incubation with the amine terminated cholesterol group was performed as described above. The method for the formation of the lipid bilayer was performed as described in Example IV, a below. The amount of mobility of the lipid bilayer was determined by FRAP analysis as described in Example IV, b below. The results of these experiments were used to determine for which amount of time the reactive groups A, were present on the surface of the PG polymer. Table 1 shows that for a time of about 92 hour after storage in water (at room temperature) the OPT treatment the contact angle remained low. After storage under air (room temperature) the contact angle remained low for about 2 hours. Thus within this time frame sterol groups could be attached to the reactive groups A to form an air-stable lipid bilayer (rBSLB).

A similar stability experiment with PA (Polyactive® 1000/70/30) showed a much lower stability of the reactive groups A (aldehyde groups) and reaction of the aldehyde groups with sterol groups preferably takes place within 5 minutes after the activation of the surface of the PA-object (see Table 1).

TABLE 1

Reactive groups A on surface

| | time (hr) in water | Contact angle (°) | rBSLB (>90% mob. fr.) after sterol coupling | time (hr) in air | Contact angle (°) | rBSLB (>90% mob. fr.) after sterol coupling |
|---|---|---|---|---|---|---|
| PG | untreated | 87 | no | untreated | 87 | no |
|    | 0.1 | 37 | yes | 0.1 | 37 | yes |
|    | 3 | 38 | yes | 0.5 | 40 | yes |
|    | 6 | 42 | yes | 1 | 42 | yes |
|    | 24 | 46 | yes | 1.5 | 46 | yes |
|    | 30 | 47 | yes | 2 | 61 | yes |
|    | 48 | 50 | yes | 4 | 85 | no |
|    | 54 | 51 | yes | 8 | 84 | no |
|    | 72 | 54 | yes | | | |
|    | 78 | 55 | yes | | | |
|    | 192 | 58 | yes | | | |
|    | 384 | 80 | no | | | |
|    | 576 | 85 | no | | | |
| PA | | | | untreated | 75 | No |
| PA | | | | 0.01 | 27 | Yes |
| PA | | | | 0.08 | 37 | Yes |
| PA | | | | 0.17 | 60 | Yes |
| PA | | | | 0.5 | 74 | No |
| PA | | | | 1 | 75 | No |

Example IV a. Formation of the Lipid Bilayer

Large unilamellar vesicles (LUVs) were prepared by extrusion (11 times) of a solution of multi laminar vesicles (MLV) through 100 nm polycarbonate membranes on an Avanti polar lipids extruder. The MLV solution was a solution of 1,2-dioleoyl-sn-glycero-3-phosphocholine (DOPC) obtained from Avanti Polar Lipids. MLVs of DOPC were generated by vortexing a rehydrated lipid cake in fresh milliQ (18MΩ) at 1 mg/mL. The lipid cake was prepared by drying 99.8 mol % DOPC and 0.2 mol % Oregon Green or Texas Red-1,2-dihexadecanoyl-sn-glycero-3-phosphoethanolamine (DHPE, Invitrogen) from organic solvent. The cake was dried under a stream of nitrogen and left to dry under vacuum for 1 hour. OPT modified polycaprolactone sheet according to example II and OPT modified and cholesterol modified polycaprolactone sheets according to example III were treated with a diluted LUV solution of 0.5 mg/mL in PBS. The sheets were incubated with the LUV solution for 45 minutes above $T_m$ of the lipids used (−20° for DOPC) to allow for vesicle adsorption and rupture to occur. Optional, to further ensure high yield of ruptured vesicles a freezing step at −80° C. was employed after the initial incubation. After extensive washing in 1× phosphate buffered saline (PBS, Sigma), the fluorescently labelled bilayer on PCL was achieved as shown by a fluorescence image of the PCL sheet.

The thickness of the DOPC layer formed on the object was 4.1 nm+/−0.7 nm as determined by force spectroscopy.

b. FRAP, Fluorescent Recovery after Photobleaching

The DOPC lipid bilayer formed according to Example IVa proved fluidic on the PCL support. The mobility was deduced by observing the diffusion occurring after a population of fluorescent lipids has been bleached, so-called recovery.

Figure 3:
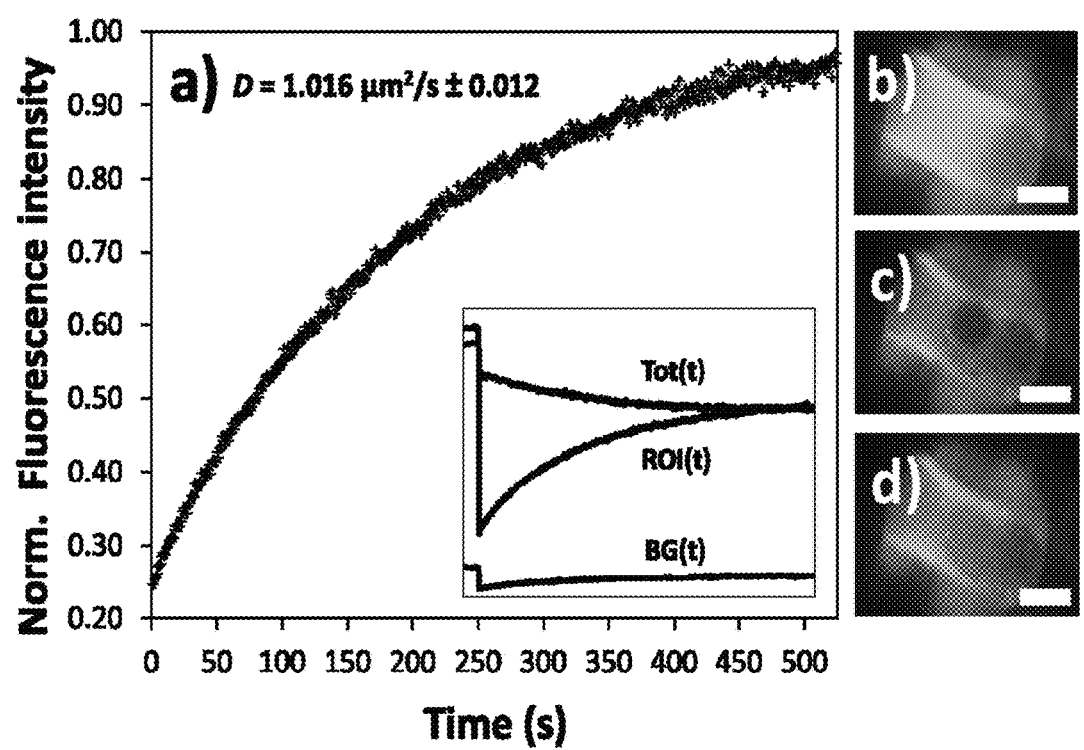
FIG. 3 shows the FRAP analysis of the lipid bilayer on a 3D PCL object.

In FIG. 3 the bilayer consisted of DOPC doped with 0.2 mol % of Oregon Green DHPE and was prepared using 100 nm LUVs. a, Fitted CSLM FRAP recovery curve using a one-component fit, $R^2$ 0.999207. A diffusion coefficient of 1.016 $\mu m^2/s \pm 0.012$ with a mobile fraction of >95% was found. The ROI, Tot and BG regions had a ω of 24 μm during bleaching and acquisition. The inset shows the complete recovery profile during a single FRAP measurement using 600 iterations at 900 ms interval. Epi-fluorescence images of b, pre bleach c, post bleach and d, after 15 minutes show recovery of fluorescence, scale bar 200 μm. Here, the field diaphragm was closed to bleach a 130 μm spot on a single fiber to qualitatively assess later diffusion of the fluorescent layer.

According to the method described above lipid bilayers were formed on PCL sheets that were treated with OPT and thereafter incubated with an amine terminated cholesterol group for 1 hour, 2 hours or 3 hours respectively. It is shown by the results in Table 2 below that by the OPT treatment in combination with the incubation with the amine terminated cholesterol group an air-stable lipid bilayer (rBSLB) can be formed with a mobile fraction of >90% as determined by FRAP analysis. When the incubation with the amine terminated cholesterol group lasts 3 hours it is shown that the mobile fraction of the air-stable lipid bilayer was reduced to about 50%. On the untreated PCL sheet and on the PCL sheet that was only treated with OPT an air-stable lipid bilayer was not formed.

TABLE 2

Lipid bilayers

| Sample | rBSLB | Mobile fraction |
|---|---|---|
| Polycaprolactone (PCL) | no | >90% |
| 400 J, no incubation of cholesterol | no | >90% |
| 400 J, 1 hr incubation of cholesterol | yes | >90% |
| 400 J, 2 hrs incubation of cholesterol | yes | >90% |
| 400 J, 3 hrs incubation of cholesterol | yes | ~50% | c. rBSLB Protein and Cell Fouling

PCL films of 0.5×0.5 cm² (Sigma) were modified on one side, while the other side remained unaltered, with a DOPC lipid bilayer formed according to the process described in Examples II, III and IVa. These films were incubated with Bovine Serum Albumin (BSA, Sigma) modified with Dylight 488 (Thermo Scientific) for 20 min. at room temperature in the dark. After the set incubation and protein desorption in SDS solution for 1 hour the BSA-Dylight488 content was quantified for determination of the non-fouling nature of the modified PCL films. The total protein adsorption decreased by about 50% after application of the bilayer. It is expected that the reduction is due to the non-fouling nature of the zwitterionic lipid bilayer. Since only half of the total surface area was treated, a high degree of protein resistance (of about 100%) can be deduced even after dehydration and rehydration of the sample i.e. 1×, 2× or 3 times sequentially. One dehydration cycle was performed by removal of all the liquids above the object and let it dry for 30 min. Afterwards PBS was added to rehydrate the lipid bilayer, all conducted at room temperature.

BSA conjugated with DyLight 488 was incubated with the substrates in PBS. The adsorbed protein was quantified with a plate reader after being desorbed in SDS solution. The inset shows adsorption data of BSA in DMEM, lacking FBS. Relative protein adsorption is presented as mean±SD (n=3) and compared using 1-way Anova with post-hoc Tukey test, *p=<0.05.

TABLE 3

BSA Adsorption

| | Protein fouling | |
|---|---|---|
| | Norm | Std |
| PCL | 1.25 | 0.14 |
| PCL Linker | 1.00 | 0.08 |
| rBSLB | −0.03 | 0.07 |
| 1x rBSLB | −0.07 | 0.03 |
| 2x rBSLB | 0.00 | 0.06 |
| 3x rBSLB | −0.01 | 0.03 | rBSLB = the lipid bilayer formed by application of a DOPC lipid on the object
PCL = polycaprolactone The BSA adsorption figures show that the attachment of the lipid bilayer to the PCL object is stable. Even after rehydration and dehydration of the sample 3 times no amendment of the BSA adsorption occurred. Further no fouling with the proteins out of the BSA occurs on the lipid bilayer. This means that the lipid bilayers will also protect the object against other forms of bio-fouling.

d. Protein Fouling on BSLB

To gain insight in the non-fouling behaviour of the BSLBs, a protein adsorption assay was performed. Here, fluorescently labelled BSA was prepared and used to quantify the amount of protein adsorbed to the samples surface. Briefly, n-hydrocysuccinimide (NHS) activated Dylight-488 was incubated with BSA and purified using spin columns following the protocol provided by the manufacturer (Thermo Scientific). BSLB modified PCL films of 0.5×0.5 cm$^2$ (Sigma) were incubated with 50 μg/mL BSA conjugates in PBS for 20 min. Subsequent washings using PBS ensured loosely bound protein to be removed. Adsorbed protein was desorbed in SDS solution for 1 h at room temperature and quantified using a plate reader (Victor, Perkin-Elmer) and a standard curve. In the case of the dehydrated BSLB the buffer was removed and the surface was exposed to air. Subsequently, PBS buffer was added to rehydrate the BSLB samples. Data are presented in Table 4 and show that upon formation of the BSLB the amount of adsorbed protein is significantly reduced.

TABLE 4

BSA adsorption

| | PCL | BSLB | 1x dehydrated BSLB | 2x dehydrated BSLB |
|---|---|---|---|---|
| BSA (ng/cm$^2$) | 37.77 ± 19.72 | 0.27 ± 0.08 | 0.17 ± 0.04 | 0.11 ± 0.01 |

Example V

Palmitoylated Peptide Synthesis a. Preparation of Palmitoylated Peptide Precursors KGG-peptides were synthesized using a microwave solid-phase peptide synthesizer (OEM). The fluorenylmethyloxycarbonylchloride (FMOC)-protected amino acids and the coupling reagents hydroxybenzotriazole (HOBT) and O-Benzotriazole-N,N,N',N'-tetramethyl-uronium-hexafluoro-phosphate (HBTU) were obtained from Multisyntech. Rink-amide resin and HOBT/HBTU coupling were used. Standard manufacturers amino acid coupling methods were adopted. With exception that the first amino acid was coupled using an initial double coupling procedure.

The peptides were synthesized using solid-phase microwave peptide synthesis.

Peptide Synthesis Reagents (Working Solutions)
Solvent: N-Methyl-2-pyrrolidone (NMP)
Resin: Rink amide (Multisynth Technology)
Deprotection solution: 20% piperidine, 0.1M HOBT in NMP
Activator: 0.5 M HBTU in NMP
Activator base: 2.0 M DIPEA in NMP
Amino acids: 0.2 M of Amino Acids, 0.3M HOBT in NMP
Amino Acid Single Coupling
1. Resin was washed ash with NMP
2. Add Deprotection, 10.0 mL.
3. Microwave step; 35 Watt, max T ~40° C., ~40 sec
4. Resin was washed with NMP
5 Add Deprotection 10.0 mL
6. Microwave step, 35 Watt, max T ~79° C., ~3 min
7. Resin was washed with NMP
8. Add Amino Acid 5.0 mL
9. Add Activator 2.0 mL
10. Add Activator Base 1.0 mL
11. Microwave step; Ser, Asp, Gly: 25 Watt, max T ~79° C., ~5 min
12. Wash NMP
Amino Acid Double Coupling
1. Resin was washed with NMP
2. Add Deprotection, 10.0 mL.
3. Microwave step; 35 Watt, max T ~40° C., ~40 sec.
4. Resin was washed with NMP
5 Add Deprotection 10.0 mL
6. Microwave step; 35 Watt, max T ~79° C., ~3 min
7. Resin was washed with NMP
8. Add Amino Acid 5.0 mL
9. Add Activator 2.0 mL
10. Add Activator Base 1.0 mL
11. Microwave step;
Arg; 0 Watt, max T ~79° C., ~30 min
Lys; 25 Watt, max T ~79° C., ~5 min
12. Add Amino Acid 5.0 mL
13. Add Activator 2.0 mL
14. Add Activator Base 1.0 mL
15. Microwave step;
Arg; 25 Watt, max T ~79° C., ~5 min
Lys; 25 Watt, max T ~79° C., ~5 min
16. Resin was washed with NMP The N-terminal KGG-R$_n$ was used to couple N-hydroxysuccinimide (NHS) activated palmitic acid. NHS-palmitate was prepared according to a literature procedure. 1:1:1 molar equivalents of palmitic acid (Sigma), NHS (Sigma) and N,N'-dicyclohexylcarbondiimide (DCC, Sigma) were stirred at 0° C. for 1 hr and left overnight at room temperature in THF. The reaction solution was filtered and the product was purified by means of recrystallization in hot methanol.

The IR analysis showed for palmitic acid the C—H stretching at 2,912 & 2,848 cm$^{-1}$ of the alkane, the O—H and —C═O stretching at 2,500-3,300 cm$^{-1}$ and 1,700 cm$^{-1}$ of the acid. The NHS-palmitate showed peaks at: Alkane, —C—H: 2,912 & 2,848 cm$^{-1}$; Ester, —C═O: 1,821 cm$^{-1}$ and —C—O—N: 1,071 cm$^{-1}$; succinimide, sym. C═O: 1,784 cm$^{-1}$, asym. C═O: 1,731 cm$^{-1}$ and asym. C—N—C: 1,212 cm$^{-1}$.

a. Preparation of Mono- and Bi-Palmitoylated Peptides

After completion of the peptide synthesis a final deprotection step was performed to yield a 'free' N-terminal amine, leaving the lysine side-group protected. On resin the peptide was reacted with 10 molar equivalents NHS-palmitate in DMF and a small amount of N,N-diisopropylethylamine (DIPEA). The NHS-palmitate was allowed to react for 5 hours. The resin was washed multiple times with DMF and DCM after that microwave cleavage using the microwave solid-phase peptide synthesizer (CEM) in a TFA/TIS/water 95/2.5/2.5 was performed according to manufactures instruction as described under Example Va. After diethyl ether precipitation the peptide conjugate was purified with HPLC and lyophilized. HPLC purification was performed using water and acetonitrile gradient supplemented with 0.1% TFA. Using ES$^+$ the [M+H]$^+$ and [M+H]$^{2+}$ peaks could be found for the fibronectin derivatives Using the lyophilized, purified 'monopal' peptides the coupling of a second NHS-palmitate to the 'free' amine of the lysine residue was performed. The reaction was conducted in DSMO/DIPEA in a 10 times molar excess of NHS-palmitate. The reaction was monitored using ES+ and stopped upon disappearance of the monopal peak, after 4 hours. The crude was washed several times with diethyl ether to remove unreacted NHS-palmitate. The DMSO fraction was diluted with milliQ and lyophilized.

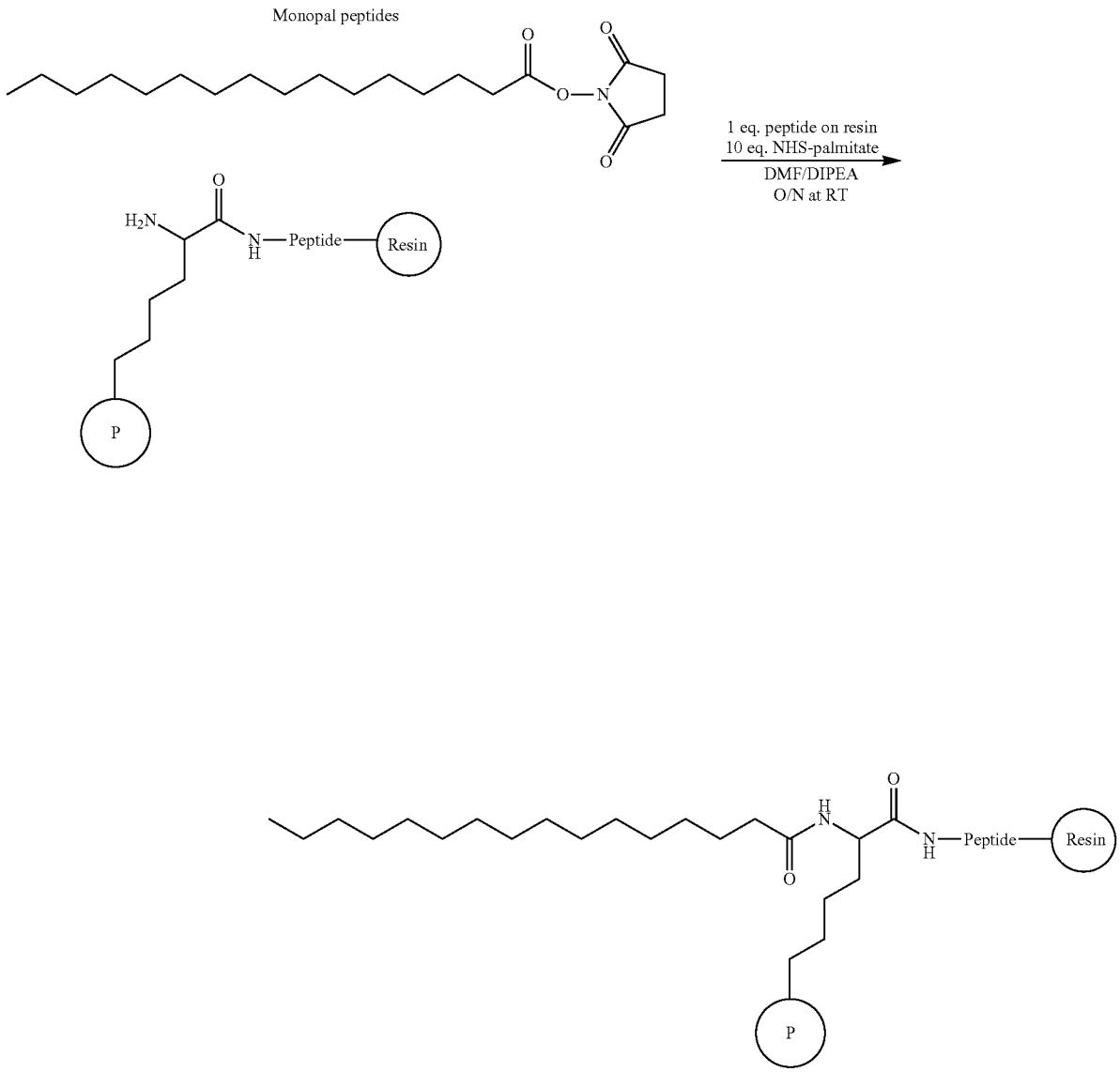

Scheme 2 Schematic representation of the preparation of mono- and bi-palmitoylated peptides -continued Bipal peptides

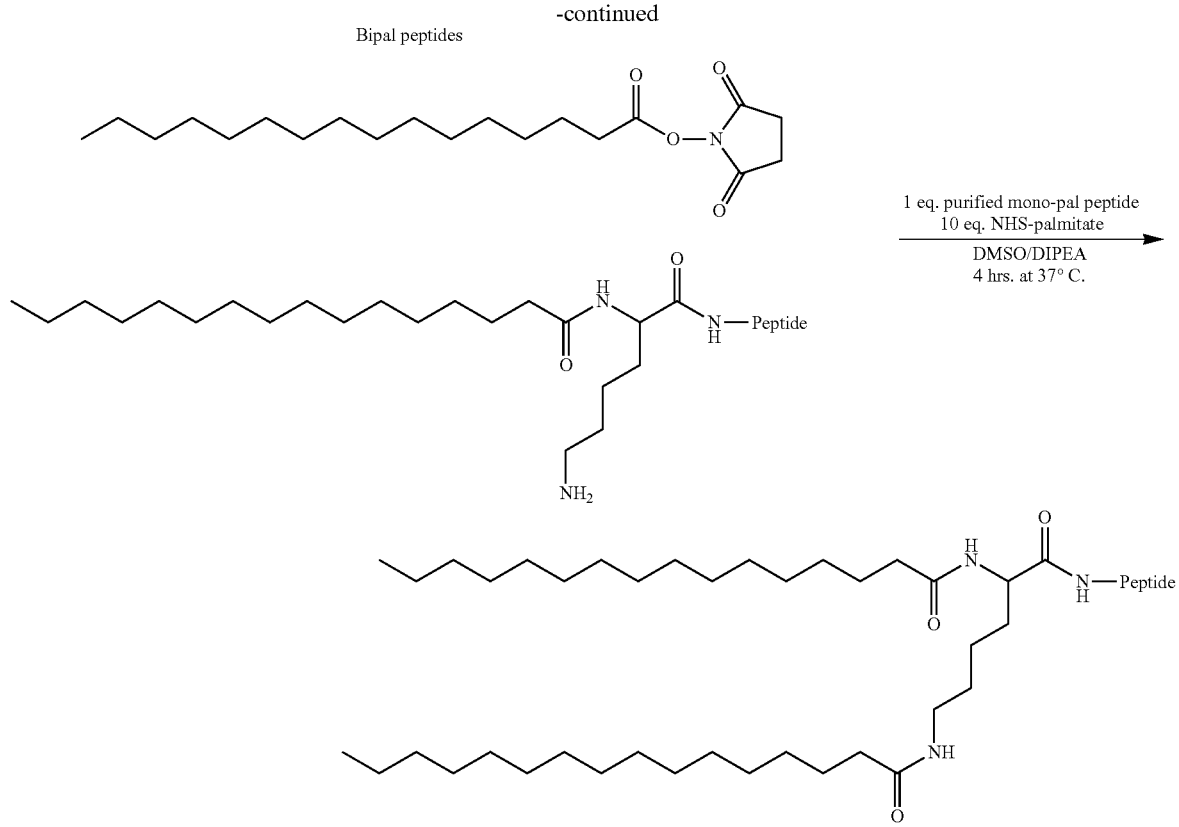

Example VI

Cell Experiments, Mesenchymal Stem Cells

PCL membranes functionalized with two different lipid bilayers were used. The functionalized PCL membranes were obtained according to the process as described in Example IVa. To test the performance of the lipid bilayers palmitoylated RGD peptides were chosen as a model system for cell adhesion. Here, the bilayer was contacted with a high concentration of peptide (10 mol %) and the effect of lipids lateral mobility on cell behavior was compared. In the figure the resulting cell size as well as cell area was deduced after two hours of incubation. The cell count decreased upon application of a bare DOPC or DSPC bilayer. However, upon doping with RGD peptides the cell count increased. When RGE control peptides were chosen, cell adhesion was suppressed. Moreover, for the gel state lipids (DSPC) the cell area was significantly higher.

TABLE 5

| | Cell Adhesion | | | |
|---|---|---|---|---|
| | Cells per mm$^2$ | | Cell area μm$^2$ | |
| | Mean | Std | Mean | Std |
| PCL | 9.0 | 6.6 | 681.4 | 148.0 |
| OPT PCL | 141.2 | 143.2 | 1437.9 | 68.7 |
| PCL Linker | 67.5 | 34.3 | 1537.0 | 445.3 |
| Liq. BSLB | 11.8 | 2.3 | 466.5 | 126.1 |
| Liq. BSLB 10% RGD | 138.7 | 79.1 | 840.7 | 73.0 |
| Liq. BSLB 10% RGE | 28.8 | 24.2 | 881.8 | 94.5 |
| Gel BSLB | 3.0 | 0.0 | 933.3 | 372.3 |

TABLE 5-continued

| | Cell Adhesion | | | |
|---|---|---|---|---|
| | Cells per mm$^2$ | | Cell area μm$^2$ | |
| | Mean | Std | Mean | Std |
| Gel BSLB 10% RGD | 244.5 | 73.4 | 1136.8 | 72.6 |
| Gel BSLB 10% RGE | 98.0 | 75.1 | 1362.9 | 185.1 |

BSLB = the lipid bilayer formed by application of a DOPC lipid (liq. BSLB) or a DSPC lipid (Gel BSLB) on the PCL membrane
PCL = polycaprolactone Immortalized Mesenchymal Stem Cells (iMSCs) were seeded in basal media for two hours at a density of 5,000 cells per cm$^2$ and washed after 30 minutes to remove loosely adherent cells.

TABLE 6

| | Cell Response | | | |
|---|---|---|---|---|
| | Norm ALP/DNA | | Norm Oli O Red/DNA | |
| | Mean | STD | Mean | STD |
| Linker | 1.00 | 0.47 | 1.00 | 0.22 |
| DOPC | 0.28 | 0.10 | 1.15 | 0.16 |
| DSPC | 0.81 | 0.02 | 0.75 | 0.11 |
| DOPC_RGD | 0.74 | 0.28 | 2.19 | 0.59 |
| DSPC_RGD | 2.05 | 1.50 | 0.84 | 0.34 |

To study the effect of lateral mobility more in detail iMSCs were cultured for a period of 1 week in adipogenic media (to promote the formation of fat cells) and in osteogenic media (to promote the formation of bone cells, both fully supplemented. It has been described that fat cell differentiation is promoted on soft surfaces while bone differentiation on stiff supports. It is postulated that mobile ligands (liquid BSLB) would approximate soft materials while immobile ligands (gel BSLB) stiff ones. To assess osteogenesis ALP was measured and corrected for DNA content. Moreover, prior to that a proliferation assay allowed us to get insight into the cell densities of the Oil O Red samples that were used to determine adipogenesis.

It can be noted that the liquid state BSLB promoted adipogenesis while the gel state BSLB promoted osteogenesis.

What is claimed is:

1. A process for the preparation of an object, supporting a lipid bilayer, comprising the steps of:
   providing an object having a surface,
   treating the surface of the object with a plasma containing active oxygen to provide the surface of the object with reactive groups A,
   covalently attaching a sterol group to the reactive groups A and
   contacting the object activated with sterol groups with a lipid solution to form a lipid bilayer.

2. The process according to claim 1, wherein the object is made of a metal, metal oxides, alloy, glass, ceramic or polymeric materials or combinations of these materials.

3. The process according to claim 1, wherein an oxygen containing RF plasma or cold plasma is used.

4. The process according to claim 1, wherein the reactive groups A are aldehyde groups.

5. The process according to claim 1, wherein the attaching of the sterol groups occurs within 2 hours from treatment of the surface of the substrate.

6. The process according to claim 1, wherein the sterol group comprises a spacer moiety, which spacer moiety reacts covalently with the reactive groups A on the surface of the object.

7. The process according to claim 6, wherein the spacer moiety comprises oligo(ethyleneglycol).

8. The process according to claim 1, wherein the amount of sterol groups attached to the object is between 0.02 $nm^{-2}$ and 5 $nm^{-2}$ determined by X-ray photoelectron spectroscopy (XPS).

9. The process according to claim 1, wherein the lipid solution comprises a phosphatidylcholine derivative.

10. The process according to claim 1, wherein the lipid bilayer is contacted with a peptide comprising at least one hydrophobic tail.

11. The process according to claim 10, wherein the peptide is RGD or PHSRN.

12. The process according to claim 1, comprising the steps of:
   a. providing the object from polycaprolactone having a surface,
   b. treating the surface of the object with an oxygen containing RF plasma or cold plasma to provide the surface of the object with reactive groups A,
   c. reacting the sterol group comprising a cholesterol covalently attached to an oligo(ethyleneglycol) spacer with reactive group A,
   d. contacting the object activated with cholesterol groups with the lipid solution comprising a phosphatidylcholine derivative to form the lipid bilayer, and
   e. contacting the lipid bilayer with a peptide RGD or PHSRN comprising one or two palmitoyl hydrophobic tails.

13. An object supporting a lipid bilayer, comprising:
   an object comprising a polymeric material,
   sterol groups covalently attached via a spacer to the polymeric material,
   a lipid bilayer surrounding the sterol groups that are covalently attached to the polymeric material and
   peptides comprising at least one hydrophobic tail attached to the lipid bilayer.

14. The object according to claim 13, wherein the polymeric material is a polyester, and wherein the spacer comprises an oligo(ethyleneglycol).

15. The object according to claim 13, wherein the lipid bilayer comprises DOPC and the peptide is RGD or PHSRN.

16. The object according to claim 14, wherein the polymeric material is polycaprolactone.

* * * * *